(12) United States Patent
Kim et al.

(10) Patent No.: US 12,168,790 B2
(45) Date of Patent: *Dec. 17, 2024

(54) METHOD OF PREPARING TOXIN

(71) Applicant: JETEMA CO., LTD., Gangwon-do (KR)

(72) Inventors: Jae Young Kim, Seoul (KR); Jeong Sun Nam, Seoul (KR); Seungho Kim, Seoul (KR); Minjoong Kim, Gyeonggi-do (KR); Wonil Lee, Gyeonggi-do (KR); Bum Jin Yun, Seoul (KR)

(73) Assignee: JETEMA CO., LTD., Gangwon-do (KR)

( * ) Notice: Subject to any disclaimer, the term of this patent is extended or adjusted under 35 U.S.C. 154(b) by 140 days.

This patent is subject to a terminal disclaimer.

(21) Appl. No.: 17/599,696

(22) PCT Filed: Mar. 12, 2020

(86) PCT No.: PCT/KR2020/003458
§ 371 (c)(1),
(2) Date: Sep. 29, 2021

(87) PCT Pub. No.: WO2020/204395
PCT Pub. Date: Oct. 8, 2020

(65) Prior Publication Data
US 2022/0195412 A1 Jun. 23, 2022

(30) Foreign Application Priority Data

Mar. 29, 2019 (KR) .................. 10-2019-0036921

(51) Int. Cl.
C12P 21/02 (2006.01)
A61K 38/48 (2006.01)
C12N 9/52 (2006.01)

(52) U.S. Cl.
CPC ........ *C12N 9/52* (2013.01); *C12Y 304/24069* (2013.01)

(58) Field of Classification Search
None
See application file for complete search history.

(56) References Cited

U.S. PATENT DOCUMENTS

2010/0086971 A1* 4/2010 Suppmann ............... C12N 1/20
435/243

FOREIGN PATENT DOCUMENTS

| CN | 102089438 A | 6/2011 |
| EP | 3950930 A1 | 2/2022 |
| JP | 2018033433 A | 3/2018 |
| KR | 10-2009-0120222 A | 11/2009 |
| KR | 1020090129362 A | 12/2009 |
| KR | 1020160127997 A | 11/2016 |
| RU | 2663586 C1 | 8/2018 |
| WO | WO2006042542 A2 | 4/2006 |
| WO | WO2009142352 A1 | 11/2009 |
| WO | WO2011008713 A1 | 1/2011 |
| WO | 2016175566 A1 | 11/2016 |
| WO | 2018200991 A1 | 11/2018 |
| WO | WO-2021124296 A1 * | 6/2021 ............... C12N 1/20 |

OTHER PUBLICATIONS

Solomon, H.M., et al., "Growth and Toxin Production by Clostridium botulinum in Sliced Raw Potatoes Under Vacuum With and Without Sulfite", Journal of Food Production, 1994, pp. 878-881, vol. 57, No. 10, Publisher: International Association of Milk, Food and Environmental Sanitarians.
Calleri De Milan, M.C., et al., "Optimization of Culture Conditions for Toxin Production of Type G Clostridium botulinum", Zbl. Bakt., 1992, pp. 161-169, vol. 277, Publisher: Gustav Fischer Verlag.
Fang, A., et al., "Production of Clostridium difficile toxin in a medium totally free of both animal and dairy proteins or digests", PNAS, 2009, pp. 13225-13229, vol. 106, No. 32.
Office Action in counterpart Russian Patent Application No. 2021128380, Aug. 19, 2022.
English Translation of Russian Office Action in counterpart Russian Patent Application No. 2021128380, Aug. 19, 2022.
Siegel, L.S., et al., "Toxin Production by Clostridium botulinum Type A Under Various Fermentation Contditions", Applied and Environmental Microbiology, 1979, pp. 606-611, vol. 38, No. 4.
Search Report in Counterpart Russian Patent Application No. 2021128380.
EESR issued in counterpart European Patent Application No. 20784897.9 on Feb. 24, 2023.
Office Action issued on Jun. 6, 2024 for Chinese Patent Application 202080034761.2.
English Translation of Office Action issued on Jun. 6, 2024 for Chinese Patent Application 202080034761.2.

* cited by examiner

*Primary Examiner* — David Steadman
(74) *Attorney, Agent, or Firm* — HULTQUIST, PLLC; Steven J. Hultquist (57) ABSTRACT

Disclosed are a medium composition for culturing *Clostridium botulinum* comprising a potato peptone, a yeast extract and glucose, and a method of preparing a botulinum toxin using the same. The medium excludes animal-derived products and major allergens, and enables the botulinum toxin-producing strain to reach the maximum growth level within a short time, thereby providing effects of shortening the production time and reducing the production cost in the botulinum toxin production process.

2 Claims, 5 Drawing Sheets

METHOD OF PREPARING TOXIN

CROSS-REFERENCE TO RELATED APPLICATIONS

This application is a United States national phase under 35 USC § 371 of International Patent Application No. PCT/KR2020/003458 filed Mar. 12, 2020, which in turn claims priority under 35 USC § 119 of Korean Patent Application No. 10-2019-0036921 filed Mar. 29, 2019. The disclosures of all such applications are hereby incorporated herein by reference in their respective entireties, for all purposes.

BACKGROUND OF THE INVENTION

Field of the Invention

The present invention relates to a medium composition for culturing *Clostridium botulinum* and a method for preparing a botulinum toxin using the same, and more specifically, to a medium composition for culturing *Clostridium botulinum* that comprises a potato peptone, a yeast extract and glucose and is capable of effectively shortening the culture time of *Clostridium botulinum* while excluding animal-derived products and major allergens, and a method for preparing a botulinum toxin using the same.

Description of the Related Art

Botulinum toxin is a neurotoxic protein produced by bacteria such as *Clostridium butyricum, Clostridium baraffi*, and *Clostridium botulinum*. Botulinum toxin blocks neuromuscular transmission and causes neuroparalytic diseases in humans and animals. In particular, botulinum toxin type A is known to be very fatal to humans. In addition to botulinum toxin type A, six other botulinum toxins types B, C1, D, E, F, G and H have been identified. Each botulinum toxin type can be distinguished by a corresponding type-specific antibody, and there is a difference in the severity of the paralysis caused thereby and the animal species affected thereby.

The molecular weight of the botulinum toxin protein molecule is about 150 kD, including a light chain of about 50 kD and a heavy chain of about 100 kD conjugated thereto. However, botulinum toxin released from *Clostridium* bacteria is released in the form of a complex of a 150 kD toxin protein with at least one non-toxin protein. For example, botulinum toxin is released as 900 kD, 500 kD and 300 kD complexes.

Botulinum toxin may be very fatal to humans, but botulinum toxin has recently been developed to treat a variety of symptoms including neuromuscular disorders characterized by skeletal muscle hyperactivity. For example, Botox° is a trademark of botulinum toxin A commercially developed by Allergan, Inc., which is used to alleviate or treat blepharospasm, strabismus, cervical dystonia and glabella (facial) wrinkles, and research is underway to develop applications suitable for other serotypes and clinically utilize the serotypes.

Botulinum toxins for clinical use are generally isolated from cell cultures. Conventionally, botulinum toxins have been mainly isolated through culture, fermentation and purification processes using animal-derived products. However, when botulinum toxin is produced using animal-derived products, there is a concern in that, when the botulinum toxin is administered to a patient, various pathogens or infectious substances derived from the animals may also be administered thereto. For example, prions may be contained in a produced botulinum toxin composition. The prion is a type of disease infection factor completely different from bacteria, viruses, fungi and parasites. The animals including humans infected with the prion undergo perforation of the brain like a sponge and death of nerve cells, resulting in loss of the corresponding brain function. Prions can generate an abnormal coformational isoform from the same nucleic acid sequence producing a normal protein, and infectivity is present during the "recruitment reaction" in which normal isomers become prion protein isoforms in the post-translational stage. Normal intrinsic cellular proteins induce misfolding into pathogenic prion structures. Creutzfeldt-Jakob disease is a rare neurodegenerative disease of human transmissable spongiform encephalopathies and the infectious substance is an abnormal isoform of the prion protein. Subjects with the Creutzfeldt-Jakob disease may be aggravated into akinetic mutism from the health condition within six months. Thus, administration with a pharmaceutical composition containing a biological agent such as botulinum toxin obtained using animal-derived products has a risk of causing a prion-mediated disease such as Creutzfeldt-Jakob disease.

In order to remove the risk, for example, attempts have been made to exclude animal-derived ingredients from a culture medium in the process of producing a botulinum toxin. As a representative example, Allergan Inc. devised a method of conducting fermentation in a medium containing soybeans as a plant-derived ingredient, instead of an animal-derived ingredient (Korean Patent Laid-open No. 10-2006-0102330), but the method has a problem in that the strain should be cultured for a long time to produce a sufficient amount of botulinum toxin.

Food allergy is an abnormal response to a digested food triggered by the immune system. Food allergy generally involves symptoms causing serious discomforts in everyday life such as hives, angioedema and atopic dermatitis, and may result in anaphylaxis, which is a serious and dangerous allergic reaction that has the potential to become life-threatening. The eight major causes of food allergy published by the FDA are milk, eggs, fish, crustaceans, nuts, peanuts, wheat and soybeans, which account for 85 to 90% of the total causes.

Accordingly, as a result of extensive efforts to develop a component capable of effectively culturing a botulinum toxin-producing strain while replacing a conventional medium containing an animal-derived ingredient and excluding possible allergens, the present inventors found that, when culturing *Clostridium butyricum* in a medium composition containing a potato peptone, a yeast extract and glucose, the culture speed can be significantly improved so that *Clostridium butyricum* can reach a maximum growth level within a very short time. Based on this finding, the present invention has been completed.

SUMMARY OF THE INVENTION

Therefore, the present invention has been made in view of the above problems, and it is an object of the present invention to provide a method for preparing a botulinum toxin using a medium composition capable of improving the growth speed of a botulinum toxin-producing strain, compared to a conventional medium composition, as a composition excluding an animal-derived product and a major allergen.

In accordance with an aspect of the present invention, the above and other objects can be accomplished by the provision of a method of preparing a botulinum toxin comprising (a) producing a botulinum toxin by culturing *Clostridium botulinum* in a medium composition for culturing *Clostridium botulinum* comprising a potato peptone, a yeast extract and glucose , and (b) recovering the botulinum toxin.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Unless defined otherwise, all technical and scientific terms used herein have the same meanings as appreciated by those skilled in the field to which the present invention pertains. In general, the nomenclature used herein is well-known in the art and is ordinarily used.

In the present invention, it was identified that, when the *Clostridium botulinum* strain was cultured in a culture medium containing a potato peptone, a yeast extract and glucose, as an culture medium which is free of animal-derived ingredients and allergens, the strain reached the maximum growth level within a very short time and the culture speed was significantly improved.

Accordingly, in one aspect, the present invention is directed to a medium composition for culturing *Clostridium botulinum*, comprising a potato peptone, a yeast extract and glucose.

The botulinum toxin-producing strain used in the present invention may be *Clostridium botulinum* or a variant thereof, most preferably *Clostridium botulinum* type A, NCTC13319, but is not limited thereto. It will be apparent to those skilled in the art that any strain capable of producing botulinum toxins can be used.

The present invention is characterized in that the medium composition comprises 2 to 5% (w/v) of the potato peptone, 0.5 to 2% (w/v) of the yeast extract and 0.75 to 1.5% (w/v) of the glucose, most preferably, the medium composition comprises 3% (w/v) of the potato peptone, 1% (w/v) of the yeast extract and 1% (w/v) of the glucose, but is not limited thereto.

Figure 7:
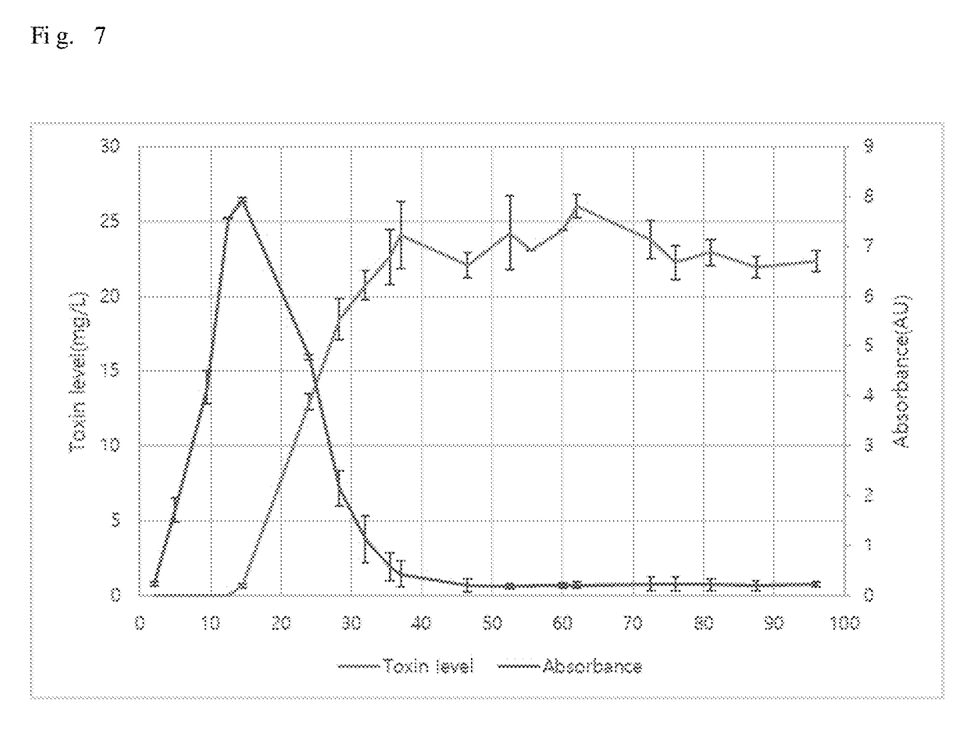
FIG. 7 shows the result of determination of the absorbance according to the toxin level and strain growth over time, while culturing *Clostridium botulinum* in the optimized medium composition of the present invention.

Meanwhile, in the present invention, it was identified that, when culturing a *Clostridium botulinum* strain using the medium composition, the culture speed increases and the recovery timing can thus be significantly shortened in the process of producing the botulinum toxin. That is, in the culture of *Clostridium botulinum* using soybean peptone, *Clostridium botulinum* exhibits the maximum growth level after 24 hours. On the other hand, *Clostridium botulinum* according to the present invention exhibits the maximum growth level in about 14 to 18 hours. Regarding the toxin recovery timing, in the case of the conventional culture of *Clostridium botulinum*, the maximum toxin production was obtained after culture for at least 48 hours, whereas in the present invention, the maximum toxin production was obtained within 48 hours culture, that is, at about 37 hours culture (see FIG. 7). The effect described above is considered to be obtained when the potato peptone is used as a peptone.

Accordingly, in another aspect, the present invention is directed to a method of preparing a botulinum toxin comprising (a) producing a botulinum toxin by culturing *Clostridium botulinum* in a medium composition for culturing *Clostridium botulinum* containing a potato peptone, a yeast extract and glucose, and (b) recovering the botulinum toxin.

In the present invention, the *Clostridium botulinum* may be *Clostridium botulinum* type A, preferably *Clostridium botulinum* type A, NCTC13319, but is not limited thereto.

In the present invention, the medium composition for culture may exclude an animal-derived product and an allergen.

In the present invention, the medium composition comprises 2 to 5% (w/v) of the potato peptone , 0.5 to 2% (w/v) of the yeast extract, and 0.75 to 1.5% (w/v) of the glucose.

The composition ratio of the ingredients as described above is a composition ratio of the components obtaining 90% of a toxin production level, obtained through a surface analysis method based on the optimization concentration setting program of the minitab program, when the toxin production level in a medium composition containing 3% (w/v) of a potato peptone, 1% (w/v) of a yeast extract and 1% (w/v) of glucose, which is the best mode of the composition ratio of the components of the present invention, is assumed to be 100%. That is, the toxin production level corresponding to 90% of the toxin production level obtained with the medium composition containing 3% (w/v) of the potato peptone, 1% (w/v) of the yeast extract and 1% (w/v) of the glucose can be obtained when 2 to 5% (w/v) of the potato peptone, 0.5 to 2% (w/v) of the yeast extract and 0.75 to 1.5% (w/v) of the glucose are contained in the medium composition.

In the present invention, the potato peptone may be present in an amount of 3% (w/v) , the yeast extract may be present in an amount of 1% (w/v), and the glucose may be present in an amount of 1% (w/v), but is not limited thereto.

In the present invention, the botulinum toxin is recovered within 48 hours after initiation of culture in step (b), preferably the botulinum toxin is recovered within 40 hours after initiation of culture in step (b).

In the present invention, the term "excluding an animal-derived ingredient" means substantially excluding an animal-derived ingredient or substantially excluding an animal protein, and specifically means that a blood-derived, bloodpooled and other animal-derived product or compound is absent or substantially absent. The term "animal" means mammals (such as humans), birds, reptiles, fish, insects, spiders or other animal species. The "animal" does not include microorganisms such as bacteria. Thus, a medium or method excluding an animal product, or a medium or method substantially excluding an animal product, which falls within the scope of the present invention, may include botulinum toxins or *Clostridium botulinum* bacteria. For example, a method excluding an animal product or a method substantially excluding an animal product means a method that substantially excludes, essentially excludes, or completely excludes an animal-derived protein such as an immunoglobulin, meat digest, meat byproduct, and milk or dairy product or digest. Thus, examples of the method excluding an animal product include a method (such as bacterial culture or bacterial fermentation method) excluding meat and dairy products or meat and dairy byproducts.

As used herein, the term "botulinum toxin" means not only a neurotoxin produced by *Clostridium botulinum* but also a botulinum toxin (or light or heavy chain) produced recombinantly by a non-*Clostridium botulinum* species. As used herein, the term "botulinum toxin" refers to botulinum toxin subtypes A, B, C, D, E, F, G and H (Weller C (15 October 2013). "New Botulinum Toxin Deemed Deadliest Substance Ever: Sniffing 13-Billionths of a Gram Can Kill". Medical Daily.) and G. As used herein, botulinum toxin also includes both a botulinum toxin complex (i.e., 300, 600 and 900 kDa complexes) as well as a pure botulinum toxin (i.e., about 150 kDa). The term "pure botulinum toxin" is defined as a botulinum toxin isolated or substantially isolated from other proteins including proteins forming the botulinum toxin complex. The pure botulinum toxin may have a purity of 95% or higher, preferably 99% or higher.

The present invention provides a medium that includes at least reduced levels of animal or dairy by-products, substantially free of animal or dairy by-products. The term "animal or dairy by-product" means a compound or a combination of compounds prepared in or by animal (excluding bacteria) cells, in vivo or in vitro. Preferred non-animal sources of medium ingredients such as proteins, amino acids and nitrogen include plants, microorganisms (such as yeasts) and synthetic compounds.

The medium according to the present invention includes, but is not limited to, a medium for fermentation of a small or large amount of *Clostridium botulinum*, a medium for the growth and culture of *Clostridium botulinum* used to inoculate into a seed (primary) medium and a fermentation (secondary) medium, and a medium used for long-term storage of *Clostridium botulinum* cultures (e.g., stock cultures).

As a specific preferred embodiment of the present invention, the medium for growth of *Clostridium botulinum* and production of botulinum toxins may include a potato-derived ingredient, preferably a potato peptone, replacing an animal-derived ingredient.

The present invention provides a method for growing *Clostridium botulinum* capable of maximizing the production of botulinum toxins within the shortest time using a medium substantially free of an animal-derived ingredient. *Clostridium botulinum* can be grown using a medium composition containing a potato peptone, instead of an animal-derived ingredient.

In a preferred embodiment of the present invention, the growth of *Clostridium botulinum* is carried out in two steps (i.e., seed growth and fermentation). Both of these steps are preferably conducted in an anaerobic environment. The seed growth is generally used to "scale-up" the amount of microorganisms from the stored culture. The purpose of the seed growth is to increase the amount of microorganisms that can be used for fermentation. In addition, the seed growth allows the relatively dormant microorganisms in the stored culture to rejuvenate and grow into an actively growing culture. In addition, the volume and amount of viable microorganisms used to inoculate into the fermentation medium can be more precisely controlled in a more actively growing culture than in the stored culture. Therefore, growth of seed culture for inoculation into a fermentation medium is preferred. In addition, several successive steps including growth in a seed medium to scale-up the amount of *Clostridium botulinum* for inoculation into a fermentation medium can be used. The growth of *Clostridium botulinum* in the fermentation step may also be carried out by direct inoculation from the stored medium.

In the fermentation step, a part or entirety of the seed medium containing *Clostridium botulinum* from the seed growth product can be used for inoculation into the fermentation medium. Preferably, about 1 to 10% of the seed medium containing *Clostridium botulinum* from the seed growth product is used for inoculation into the fermentation medium. The fermentation is used to produce the largest amount of microorganisms in a large-scale anaerobic environment.

The botulinum toxin contained in the culture of the strain cultured by the method may be isolated and purified using protein purification methods known to those skilled in the art of protein purification.

The growth of *Clostridium botulinum* can be carried out in one or more steps. Preferably, growth proceeds in two steps. In the first step, seed growth, *Clostridium botulinum* is suspended in the medium composition according to the invention and cultured at 34±1° C. under an anaerobic environment for 10 to 24 hours. Preferably, seed growth is carried out for about 14 hours. It is also preferred that growth in the seed medium at any step does not cause cell autolysis prior to inoculation of the final growth product in the seed medium with the fermentation medium.

Subsequently, in order to further grow *Clostridium botulinum* and recover the botulinum toxin, the second step, fermentation, is performed by inoculating the medium composition of the present invention using part or all of the seed-grown medium. After inoculation, *Clostridium botulinum* is also cultured at 34±1° C. under an anaerobic environment for about 4 days and the growth thereof is monitored by measuring the optical density (OD) of the medium. Preferably, in the fermentation step using the medium composition according to the present invention, the maximum growth level is obtained after about 14 and 18 hours, the cells are lysed and the OD value decreases, whereby the botulinum toxin is recovered from the *Clostridium botulinum* within 48 hours, more preferably within 40 hours, after incubation in the fermentation step.

In a preferred embodiment of the present invention, when the culture of *Clostridium botulinum* is stored at 4° C. for long-term storage of *Clostridium botulinum* and coming inoculation of the seed medium, *Clostridium botulinum* is preferably stored in a storage medium (3% of potato peptone, 1% of yeast extract, of 1% glucose and 25% of glycerol) in order to keep the medium substantially free of animal by-products throughout the production of botulinum toxin.

EXAMPLE

Hereinafter, the present invention will be described in more detail with reference to examples. However, it will be obvious to those skilled in the art that these examples are provided only for illustration of the present invention and should not be construed as limiting the scope of the present invention.

Example 1

Sample Preparation and Bacterial Culture

1-1. Sample Preparation

The botulinum strain used in the present invention is *Clostridium botulinum* type A, NCTC13319 and the samples used to prepare the media of the experimental group and the control group are as follows: Phytone peptone (BD, 211906), Tryptone (BD, 211705), Yeast extract (BD, 212750), Potato peptone E210 (Organotechnie, 19425), Pea peptone A482 (Organotechnie, AI275), Plant peptone E1 (Organotechnie, 19025), Select phytone UF (BD, 210931), Peptone from soybean (Sigma, 70178), Hy-Soy (Kerry, 5X59022), Hy-peptone (Kerry, 5X01111), Soy peptone A2SC (Organotechnie, 19649), Soy peptone A3SC (Organotechnie, 19685), Soy peptone E110 (Organotechnie, 19885), Soy peptone K200 (Organotechnie, 19749), Glucose (Sigma, G5767), Sodium thioglycolate (Sigma, 10632), Purified water (Ultrapure water or water with quality equal to or higher than ultrapure water).

1-2. Bacterial Culture

One vial containing the *Clostridium botulinum* strain stored in a cryogenic freezer was thawed in a 37° C. incubator for 30 minutes. The *Clostridium botulinum* strain was homogenized 3 to 5 times in BSC, 0.1 mL of the homogenized *Clostridium botulinum* strain was inoculated into a medium and were then cultured at 34±1° C. in an anaerobic incubator. After the culture, $OD_{600}$ was measured using a spectrophotometer.

1-3. Toxin Level Measurement

The level of toxin was measured by the test method of Botulinum Neurotoxin Type A DuoSet ELISA (R&D system) controlled according to the instructions of the manufacturer. 100 μL of a capture antibody prepared by dilution in PBS was seeded into each well of a 96-well microplate and coated for 16 hours or more, and washing each well with a wash buffer was repeated three times in total. Each well was blocked with a reagent diluent and was then washed 3 times in total with a wash buffer.

After the culture was completed, the culture solution was sterilized using a 0.2 pm syringe filter, diluted, added in an amount of 100 μL to each well and allowed to react for 2 hours, and then washing each well with a wash buffer was repeated a total of three times. 100 μL of a detection antibody dilution was added to each well and allowed to react for 2 hours, and washing each well with a wash buffer was repeated a total of 3 times. 100 μL of a streptavidin-HRP dilution was added to each well and allowed to react for 20 minutes, and washing each well with a wash buffer was repeated a total of 3 times. 100 μL of a substrate solution was added to each well and allowed to react for 20 minutes, and 50 μL of a stop solution was added to each well and appropriately shaken to stop the enzyme reaction. 450 nm absorbance was measured in each well using a microplate reader.

Example 2

Selection of Peptone for TPYG Medium Replacement

The TPYG medium containing a casein peptone, a soy peptone, a yeast extract, glucose and sodium-thioglycolate, which has been commonly used as a conventional medium for producing a botulinum toxin, was attempted to replace with a PYG medium including a peptone, a yeast extract, glucose and sodium-thioglycolate.

Regarding the peptone, a variety of candidates including plant peptone were selected and a plant-derived medium having a similar toxin production to a TYPG medium was primarily selected among a soy-derived medium and other plant-derived medium.

2-1. Comparative Example

Preparation of TPYG Medium

The phytone peptone, tryptone, yeast extract and sodium thioglycolate were weighed as 2 g, 1 g, 1 g, and 0.1 g, respectively, using a weighing dish, and 50 mL of purified water was added to a 250 mL beaker, and the weighed medium ingredients were added thereto and stirred until the ingredients were dissolved completely. The pH was adjusted to 7.2 with 1N NaOH, the medium of the beaker was transferred to a 100 mL mass cylinder, purified water was added thereto to adjust the final liquid level to 95 mL, and then the prepared medium and a magnetic bar were transferred to a 100 mL glass bottle and the lid was closed.

Glucose was weighed as 1 g using a weighing dish, and the weighed glucose was put into a 15 mL conical tube containing approximately 3 mL of purified water and vortexed to dissolve sufficiently the glucose, and then purified water was added to the conical tube to adjust the final solution level to 5 mL.

The lid of the glass bottle was slightly opened, and the glass bottle was wrapped with foil and sterilized in an autoclave at 121° C. for 20 minutes. The sterilized medium and glucose were sufficiently cooled in BSC and then glucose was transferred to the medium and mixed.

2-2. Experimental Example

Preparation of PYG Medium

The 12 medium ingredients shown in Table 1 were weighed and dissolved in 50 mL of purified water, the pH was adjusted to 7.2 with 1N NaOH, purified water was added to adjust the final liquid level as shown in Table 1, and the prepared medium and a magnetic bar were transferred to a 100 mL glass bottle and the lid thereof was closed.

TABLE 1

| Medium name | Ingredient (g) | | Final liquid level (mL) |
|---|---|---|---|
| | Peptone | Yeast extract | |
| PYG1 | Phytone peptone | 3 | 1 | 95 mL |
| PYG2 | Potato peptone E210 | 3 | | 95 mL |
| PYG3 | Pea peptone A482 | 3 | | 95 mL |
| PYG4 | Plant peptone E1 | 3 | | 95 mL |
| PYG5 | Select phytone UF | 3 | | 95 mL |
| PYG6 | Peptone from soybean | 3 | | 95 mL |

TABLE 1-continued

| Medium name | Peptone | Yeast extract | Final liquid level (mL) |
|---|---|---|---|
| PYG7 | Hy-soy | 3 | 95 mL |
| PYG8 | Hy-peptone | 3 | 95 mL |
| PYG9 | Soy peptone A2SC | 3 | 95 mL |
| PYG10 | Soy peptone A3SC | 3 | 95 mL |
| PYG11 | Soy peptone E110 | 3 | 95 mL |
| PYG12 | Soy peptone K200 | 3 | 95 mL |

Glucose was weighed as 13 g with a weighing dish and the weighed glucose was dissolved in 65 mL of purified water. The prepared glucose solution was transferred to a 100 mL glass bottle and the lid was closed.

The prepared medium and glucose were sterilized at 121° C. for 20 minutes, the sterilized medium and glucose were sufficiently cooled in BSC, and 5 mL of the glucose solution was transferred to each medium and mixed.

2-3. Pepton Selection

The *Clostridium botulinum* strain was cultured in the medium prepared in Example 2-1 or Example 2-2 in the same manner as in Example 1-2, the $OD_{600}$ value was determined at the end of the culture, and the toxin production level was determined by ELISA in the same manner as in 1-3.

TABLE 2

| Medium name | TPYG | PYG1 | PYG2 | PYG3 | PYG4 |
|---|---|---|---|---|---|
| $OD_{600}$ | 0.437 | 0.463 | 0.385 | 0.309 | 0.013 |
| Toxin level (mg/L) | 22.7 | 21.5 | 25.4 | 2.7 | 15.6 |
| Toxin level (relative value) | 100 | 94.7 | 111.9 | 11.9 | 68.7 |

| Medium name | TPYG | PYG5 | PYG6 | PYG7 | PYG8 |
|---|---|---|---|---|---|
| $OD_{600}$ | 0.447 | 0.360 | 0.372 | 0.414 | 0.532 |
| Toxin level (mg/L) | 28.8 | 27.0 | 16.6 | 18.5 | 18.5 |
| Toxin level (relative value) | 100 | 93.8 | 57.6 | 64.2 | 64.2 |

| Medium name | TPYG | PYG9 | PYG10 | PYG11 | PYG12 |
|---|---|---|---|---|---|
| $OD_{600}$ | 0.396 | 0.147 | 0.526 | 1.980 | 2.120 |
| Toxin level (mg/L) | 27.3 | 17.2 | 8.7 | 15.9 | 7.2 |
| Toxin level (relative value) | 100 | 63.0 | 31.9 | 58.2 | 26.4 |

As a result, $OD_{600}$ and toxin production level after completion of the culture were shown in Table 2, and three mediums (PYG1, PYG2, and PYG5) showed similar toxin levels and maximum strain dissolution, and thus $OD_{600}$ of less than 1, compared to the TPYG medium. These results were verified again through repeated tests. As can be seen from Table 3, PYG1, PYG2 and PYG5 showed similar toxin production levels to TPYG in the repeated tests as well. Among them, the PYG2 medium excluding an animal ingredient and a major allergen was used to obtain the best medium composition.

TABLE 3

| Medium name | TPYG | PYG1 | PYG2 | PYG5 |
|---|---|---|---|---|
| $OD_{600}$ | 0.541 | 0.514 | 0.650 | 0.433 |
| Toxin level (mg/L) | 27.4 | 28.4 | 24.7 | 22.3 |
| Toxin level (relative value) | 100 | 103.6 | 90.1 | 81.4 |

Example 3

Medium Composition Optimization

In order to find the optimal concentrations of potato peptone, yeast extract and glucose determined through a medium screening test, a concentration range test was conducted through DoE and the optimum composition was determined based on the results of factor experiments, center point experiments and axial point experiments.

3-1. Factor Experiment

Factor experiments were conducted using medium ingredients including ingredients with eight concentration ranges as shown in Table 4. The medium was prepared in the same manner as 2-2 using the ingredients included in Table 4, and the *Clostridium botulinum* strain was cultured in the prepared medium in the same manner as in Example 1-2, the $OD_{600}$ value at the end of the culture was determined and the toxin production level was determined through ELISA in the same manner as in 1-3.

TABLE 4

| Medium name | Potato peptone E210 (g) | Yeast Extract (g) | Glucose (mL) | Final liquid level (mL) |
|---|---|---|---|---|
| Factor experiment 1 | 2 | 0.5 | 10 | 90 |
| Factor experiment 2 | 5 | 0.5 | 2.5 | 97.5 |
| Factor experiment 3 | 2 | 2 | 2.5 | 97.5 |
| Factor experiment 4 | 5 | 2 | 10 | 90 |
| Factor experiment 5 | 2 | 0.5 | 2.5 | 97.5 |
| Factor experiment 6 | 5 | 2 | 2.5 | 97.5 |
| Factor experiment 7 | 5 | 0.5 | 10 | 90 |
| Factor experiment 8 | 2 | 2 | 10 | 90 |

Figure 1:
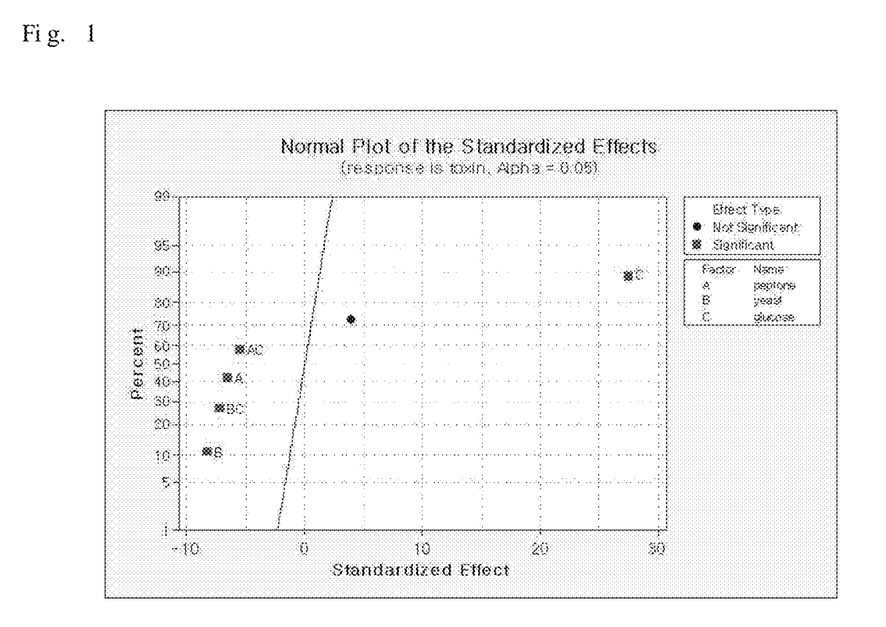
FIG. 1 shows the result of normal distribution analysis based on results of factor experiments conducted within eight concentration ranges on components according to the present invention.
Figure 2:
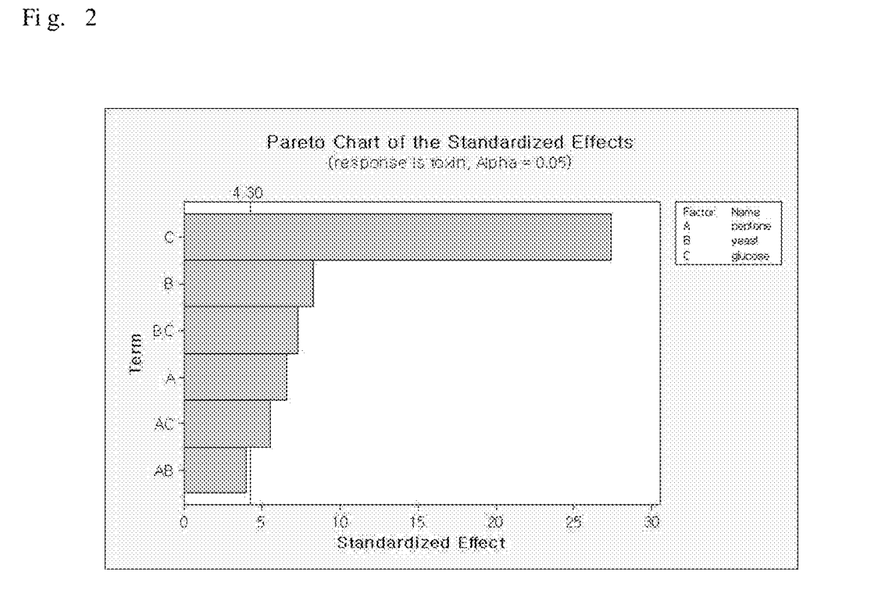
FIG. 2 shows the result of pareto analysis based on results of factor experiments conducted within eight concentration ranges on components according to the present invention.

As a result, $OD_{600}$ and toxin levels were determined as shown in Table 5. As a result of the normal distribution analysis based on the same, analysis including primary and secondary interactions while excluding ternary interaction showed that the remaining factors except for the peptone*glucose interaction in the first-order and second-order terms of peptone, yeast and glucose are significant in the toxin production level (FIG. 1), and Pareto analysis also showed the same results as the normal distribution analysis (FIG. 2).

TABLE 5

| Medium name | Medium composition | $OD_{600}$ | Toxin level (mg/L) |
|---|---|---|---|
| Factor experiment 1 | Potato peptone 2% Yeast extract 0.5% Glucose 2% | 4.560 | 20.0 |
| Factor experiment 2 | Potato peptone 5% Yeast extract 0.5% Glucose 0.5% | 0.805 | 3.0 |
| Factor experiment 3 | Potato peptone 2% Yeast extract 2% Glucose 0.5% | 0.447 | 3.0 |
| Factor experiment 4 | Potato peptone 5% Yeast extract 2% Glucose 2% | 7.600 | 9.6 |
| Factor experiment 5 | Potato peptone 2% Yeast extract 0.5% Glucose 0.5% | 0.267 | 5.2 |
| Factor experiment 6 | Potato peptone 5% Yeast extract 2% Glucose 0.5% | 0.838 | 4.5 |
| Factor experiment 7 | Potato peptone 5% Yeast extract 0.5% Glucose 2% | 6.350 | 14.3 |
| Factor experiment 8 | Potato peptone 2% Yeast extract 2% Glucose 2% | 5.080 | 13.0 |

3-2. Center Point Experiment

Potato peptone E210, yeast extract and sodium thioglycolate for a medium for center point experiments were weighed as 24.5 g, 8.75 g, and 0.7 g using a weighing dish, respectively, 550 mL of purified water was put in a 1 L beaker, and the weighted ingredients were stirred therein until they were completely dissolved. The pH was adjusted to 7.2 with 1N NaOH, the medium of the beaker was transferred to a 1 L mass cylinder, purified water was added thereto to adjust the final liquid level to 656.25 mL, and then the final liquid was transferred to a 1 L beaker and stirred for about 5 minutes. The medium was transferred in 93.75 mL to each of a total of six 100 mL glass bottles, a magnetic bar was injected into the glass bottle and the lid was closed, and each medium was designated as any one of center points 1 to 6.

Glucose was weighed as 8g using a weighing dish and the weighed glucose was completely dissolved in 40 mL of purified water.

The prepared medium and glucose were sterilized at 121° C. for 20 minutes, the sterilized medium and glucose were sufficiently cooled in BSC, and 6.25 mL of the glucose solution was transferred and mixed with each medium.

The *Clostridium botulinum* strain was cultured in the medium thus prepared in the same manner as in Example 1-2, the $OD_{600}$ value was determined at the end of the culture, and toxin production level was determined by ELISA in the same manner as in 1-3.

TABLE 6

| Medium name | Medium composition | $OD_{600}$ | Toxin level (mg/L) |
|---|---|---|---|
| Center point 1 | Potato peptone 3.5% Yeast extract 1.25% Glucose 1.25% | 3.360 | 20.2 |
| Center point 2 | Potato peptone 3.5% Yeast extract 1.25% Glucose 1.25% | 1.630 | 21.1 |

TABLE 6-continued

| Medium name | Medium composition | $OD_{600}$ | Toxin level (mg/L) |
|---|---|---|---|
| Center point 3 | Potato peptone 3.5% Yeast extract 1.25% Glucose 1.25% | 4.810 | 16.4 |
| Center point 4 | Potato peptone 3.5% Yeast extract 1.25% Glucose 1.25% | 4.300 | 16.2 |
| Center point 5 | Potato peptone 3.5% Yeast extract 1.25% Glucose 1.25% | 4.830 | 15.9 |
| Center point 6 | Potato peptone 3.5% Yeast extract 1.25% Glucose 1.25% | 5.010 | 15.1 |

The center point experiment of one concentration was repeated 6 times, and the results were shown in Table 6. When determining the presence or absence of the curve of the graph based on the results of the center point experiments, the p-value was 0.001, which is less than 0.05, which is a criterion that is determined to be significant. This means that the curve is present, and an additional test to conduct surface analysis was performed.

TABLE 7

Analysis of Variations for toxin (coded units)

| Source | DF | Seq S | Adj SS | Adj MS | F | P |
|---|---|---|---|---|---|---|
| Main Effects | 3 | 243.548 | 243.548 | 81.182 | 287.85 | 0.003 |
| peptone | 1 | 12.103 | 12.103 | 12.103 | 42.92 | 0.023 |
| yeast | 1 | 19.489 | 19.489 | 19.489 | 69.03 | 0.014 |
| glucose | 1 | 211.974 | 211.974 | 211.974 | 751.81 | 0.001 |
| 2-Way Interactions | 3 | 27.870 | 27270 | | 32.94 | 0.030 |
| peptone * yeast | 1 | 4.381 | 4.31 | 4.381 | 15.53 | 0.059 |
| peptone * glucose | 1 | 8.528 | 8.528 | 8.528 | 30.24 | 0.032 |
| yeasr * glucose | 1 | 14.980 | 14.980 | 14.980 | 53.05 | 0.018 |
| Curvature | 1 | 213.629 | 213.629 | 213.629 | 757.48 | 0.001 |
| Residual Error | 2 | 0.584 | 0.584 | 0.282 | | |
| Lack of Fit | 1 | 0.211 | 0.211 | 0.211 | 0.60 | 0.581 |
| Pure Error | 1 | 0.353 | 0.353 | 0.353 | | |
| Total | 9 | 485.609 | | | | |

3-3. Axial Point Experiment

Six medium ingredients for a medium for the axial point experiment were weighed as shown in Table 8 and dissolved in 50 mL of purified water, the pH was adjusted to 7.2 with 1N NaOH, and purified water was added thereto to adjust the final liquid level as shown in Table 8. Each prepared medium and magnetic bar were transferred to a 100 mL glass bottle and the lid was closed.

TABLE 8

| | Ingredient | | | |
|---|---|---|---|---|
| Medium name | Potato peptone E210 (g) | Yeast Extract (g) | Glucose (mL) | Final liquid level (mL) |
| Axial point 1 | 3.5 | 1.25 | 12.5 | 87.5 |
| Axial point 2 | 1 | 1.25 | 6.25 | 93.75 |
| Axial point 3 | 6 | 1.25 | 6.25 | 93.75 |
| Axial point 4 | 3.5 | 0.025 | 6.25 | 93.75 |

TABLE 8-continued

| Medium name | Ingredient | | | Final liquid level (mL) |
|---|---|---|---|---|
| | Potato peptone E210 (g) | Yeast Extract (g) | Glucose (mL) | |
| Axial point 5 | 3.5 | 2.5 | 6.25 | 93.75 |
| Axial point 6 | 3.5 | 1.25 | 0.125 | 99.875 |

Glucose was weighed as 8 g using a weighing dish and the weighed glucose was completely dissolved in 40 mL of purified water. The prepared medium and glucose were sterilized in an autoclave at 121° C. for 20 minutes, the sterilized medium and glucose were sufficiently cooled in BSC and then the glucose solution was added in an amount shown in Table 8 to each medium.

The *Clostridium botulinum* strain was cultured in the medium thus prepared in the same manner as in Example 1-2, the $OD_{600}$ value was determined at the end of the culture, and toxin production level was determined by ELISA in the same manner as in 1-3. As a result, the axial point value was determined as shown in Table 9.

TABLE 9

| Medium name | Medium composition | $OD_{600}$ | Toxin level (mg/L) |
|---|---|---|---|
| Axial point 1 | Potato peptone 3.5% Yeast extract 1.25% Glucose 2.5% | 5.53 | 7.2 |
| Axial point 2 | Potato peptone 1% Yeast extract 1.25% Glucose 1.25% | 2.550 | 12.8 |
| Axial point 3 | Potato peptone 6% Yeast extract 1.25% Glucose 1.25% | 0.416 | 20.0 |
| Axial point 4 | Potato peptone 3.5% Yeast extract 0.025% Glucose 1.25% | 2.240 | 8.1 |
| Axial point 5 | Potato peptone 3.5% Yeast extract 2.5% Glucose 1.25% | 0.447 | 21.2 |
| Axial point 6 | Potato peptone 3.5% Yeast extract 1.25% Glucose 0.025% | 0.986 | 0.3 |

3-4. Optimal Concentration Analysis through Surface Analysis

Figure 3:
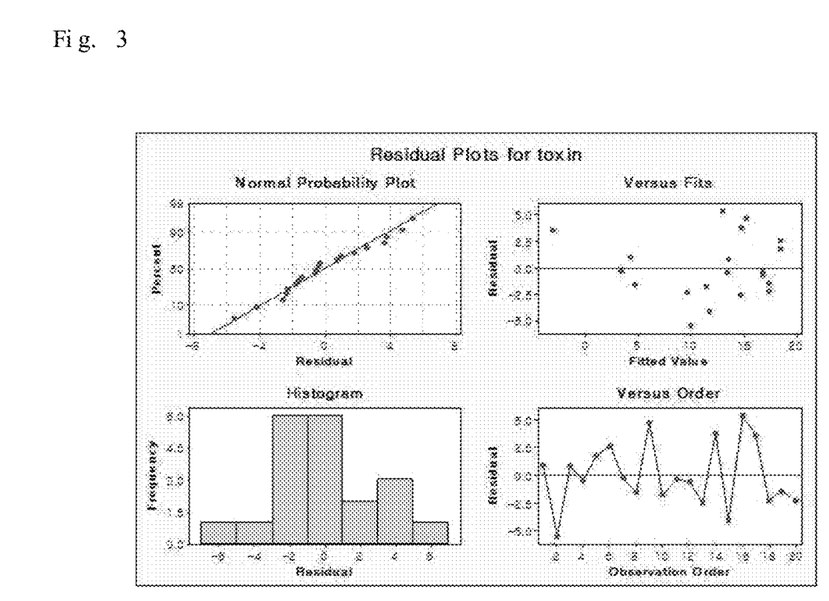
FIG. 3 shows the result of model suitability analysis based on the results of factor experiments, center point experiments and axial point experiments on the components according to the present invention.

The surface analysis was conducted based on the results of the factor experiment, center point experiment and axial point experiment. For the model suitability analysis, normal probability plots, histograms, plots of residuals versus the fitted values and plots of residuals versus the order were analyzed. The normal probability plot was determined as a straight line, the histogram appeared in the form of a normal distribution, and plots of residuals versus the fitted values and plots of residuals versus the order had no pattern. Based on these, the selected model was determined suitable (FIG. 3).

Figure 4:
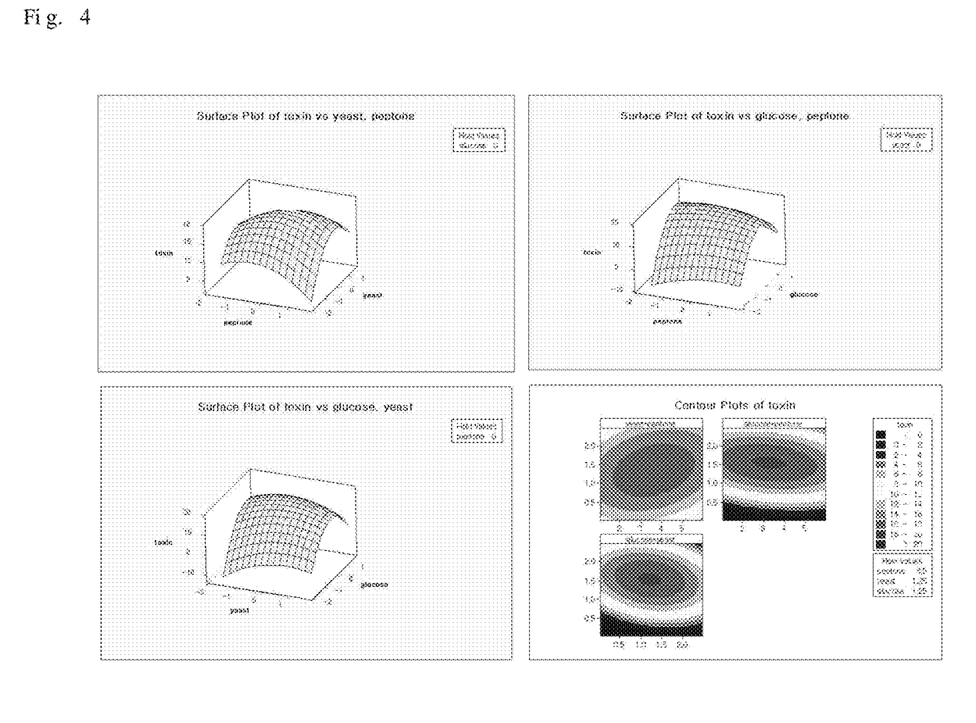
FIG. 4 shows the result of surface analysis based on the results of factor experiments, center point experiment and axial point experiments conducted on the components according to the present invention.
Figure 5:
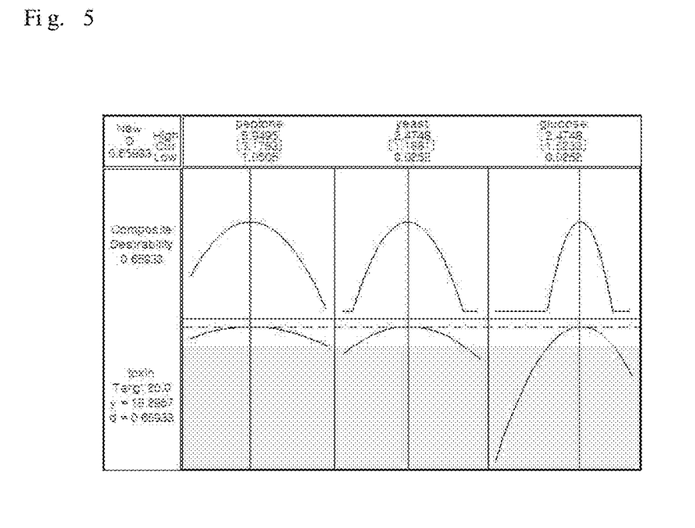
FIG. 5 shows the result of determination of the optimal ratio based on the results of surface analysis on the components according to the present invention.

The result was analyzed using surface analysis to determine the culture composition, the result is shown in FIG. 4, and the optimal ratio was calculated based on the result as shown in FIG. 5 and the optimal concentration obtained from the optimal ratio was summarized in Table 10.

TABLE 10

| Ingredient name | Potato peptone | Yeast extract | Glucose |
|---|---|---|---|
| Optimum concentration (%) | 3% | 1% | 1.5% |

3-5. Determination of Optimum Composition Ratio

Figure 6:
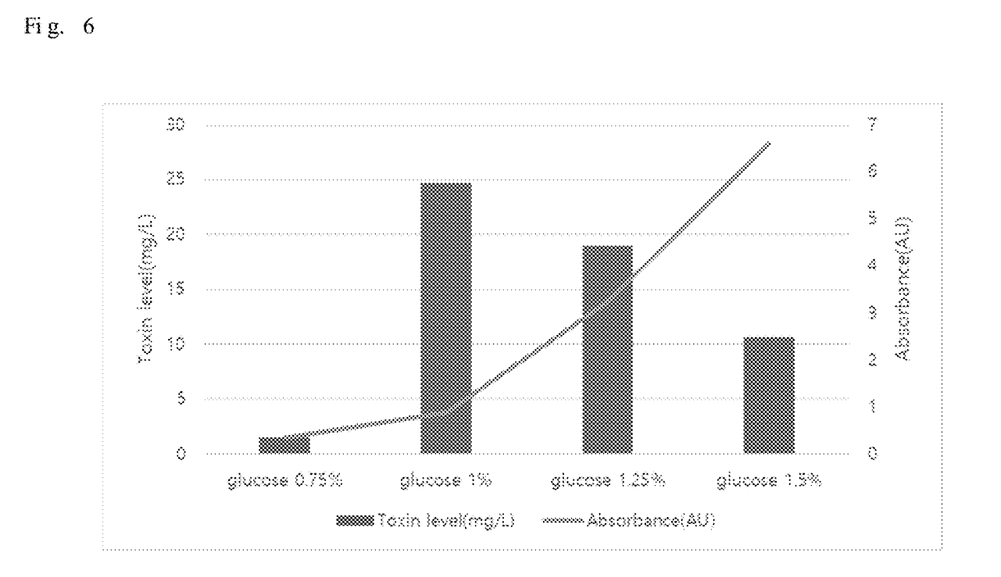
FIG. 6 shows the result of determination of the absorbance according to the toxin level and strain growth with regard to a variable glucose concentration in the optimal ratio according to the present invention.

The optimal concentration set through the surface analysis method was based on the toxin production level, and the final target was to achieve a composition having the highest toxin production level and the concentration of $OD_{600}$ after incubation of 1 or less. Thus, the optimum culture composition was obtained by changing the glucose concentration considered to have the greatest effects on toxin production level and $OD_{600}$ to 0.75, 1, 1.25, 1.5%, and the results are shown in Tables 11 and FIG. 6. The optimal medium composition was determined as 3% potato peptone, 1% yeast extract and 1% glucose.

TABLE 11

| Medium name | Medium composition | $OD_{600}$ | Toxin level (mg/L) |
|---|---|---|---|
| 0.75% | Potato peptone 3% Yeast extract 1% Glucose 0.75% | 0.343 | 1.500 |
| 1% | Potato peptone 3% Yeast extract 1% Glucose 1% | 0.877 | 24.72 |
| 1.25% | Potato peptone 3% Yeast extract 1% Glucose 1.25% | 3.230 | 18.95 |
| 1.5% | Potato peptone 3% Yeast extract 1% Glucose 1.5% | 6.580 | 10.65 |

Example 4

Strain Culture Experiment According to Optimum Culture Composition

One vial containing the *Clostridium botulinum* strain stored in a cryogenic freezer was thawed in a 37° C. incubator for 30 minutes. The *Clostridium botulinum* strain was homogenized 3 to 5 times in BSC, 1 mL of the homogenized *Clostridium botulinum* strain was inoculated into 100 mL of a PYG medium in a 2 L cell bag and was then cultured at 34±1° C. in an incubator (WAVE25). 100 mL of the strain culture was inoculated into 5 L of a PYG medium before the strain autolysis between 10 to 24 hours. Then, the absorbance at a wavelength of 600 nm and the toxin level were measured over time. Only the culture solution was recovered from each sample using a 0.2 μm antibacterial filter, and then the toxin level was measured in the same manner as in Example 1-3.

The results of measuring the change in OD and the toxin production level over time while culturing using the culture composition set as described above showed that the culture composition according to the present invention enables $OD_{600}$ of the strain culture to reach the maximum value within about 14 to 15 hours, and thus can significantly shorten the culture time compared to a conventional *Clostridium botulinum* medium composition, and that the maximum toxin production level was obtained after about 28 hours at 35° C. and after 37 hours at 33° C.

Example 5

Comparison in Culture Effect between Optimum Culture Composition and other Culture Compositions The culture effect, when soy peptone and the range other than the optimum composition ratio derived in Example 3 is used, were determined. For this purpose, each culture medium was prepared in accordance with the composition ratio shown in Table 12 and the culture effect thereof was determined. As a result, as can be seen from Table 13, the experimental group was advantageous in terms of toxin production level or cell culture time compared to Comparative Example. Specifically, in the case of using the potato peptone in Comparative Example 1, the time taken to reach the maximum cell mass was significantly shortened, but the maximum toxin production at the corresponding composition ratio was found to be much less than the experimental group. On the other hand, in the case of using the soy peptone in Comparative Example 2, the time taken to reach the maximum cell mass was found to take much longer than the experimental group.

TABLE 12

|  | Glucose | Yeast extract | Peptone |
| --- | --- | --- | --- |
| Experimental group | 1 | 1 | 3 (potato) |
| Comparative Example 1 | 1 | 0.1 | 1 (potato) |
| Comparative Example 2 | 1 | 1 | 3 (soy) |

TABLE 13

|  | Maximum cell mass (AU) | Time taken to reach maximum cell mass | Maximum toxin production (mg/L) | Time taken to reach maximum toxin production |
| --- | --- | --- | --- | --- |
| Experimental group | 7.92 | 14 h | 24.8 | 37 h |
| Comparative Example 1 | 2.74 | 21 h | 8.52 | 47 h |
| Comparative Example 2 | 7.64 | 31 h | 18.25 | 52 h |

INDUSTRIAL AVAILABILITY

According to the present invention, botulinum toxin, which is produced by excluding animal-derived ingredients and major allergens, can prevent transmissible spongiform encephalopathy caused by the accumulation of abnormal prion proteins, and adverse reactions caused by allergic reactions (tares, angioedema, atopic dermatitis, anaphylaxis), when the botulinum toxin prepared by the present invention administered to the human body. In addition, when potato peptone is used to exclude animal-derived ingredients and major allergens, the botulinum toxin-producing strain can be induced to reach the maximum growth level within a short time, and thus there are effects of shortening the production time and reducing the production cost in the botulinum toxin production process.

Although specific configurations of the present invention have been described in detail, those skilled in the art will appreciate that this description is provided to set forth preferred embodiments for illustrative purposes and should not be construed as limiting the scope of the present invention. Therefore, the substantial scope of the present invention is defined by the accompanying claims and equivalents thereto.

What is claimed is:

1. A method of preparing a botulinum toxin comprising:
   (a) producing a botulinum toxin by culturing *Clostridium botulinum* type A in a medium composition for culturing *Clostridium botulinum* comprising 3% (w/v) of a potato peptone, 1% (w/v) of a yeast extract and 1% (w/v) glucose; and
   (b) recovering the botulinum toxin within 40 hours after initiation of culture;
   wherein the botulinum toxin has a higher yield than when phytone peptone is used as the peptone source.

2. The method according to claim 1, wherein the medium composition for culture excludes an animal-derived product and an allergen.

* * * * *

UNITED STATES PATENT AND TRADEMARK OFFICE
CERTIFICATE OF CORRECTION

| | |
|---|---|
| PATENT NO. | : 12,168,790 B2 |
| APPLICATION NO. | : 17/599696 |
| DATED | : December 17, 2024 |
| INVENTOR(S) | : Jae Young Kim et al. |

It is certified that error appears in the above-identified patent and that said Letters Patent is hereby corrected as shown below:

In the Specification

Column 1, Line 53, "Botox⁽ʳ⁾" should be -- Botox® --.

Column 4, Lines 23-29, "Accordingly, in another aspect, the present invention is directed to a method of preparing a botulinum toxin comprising (a) producing a botulinum toxin by culturing *Clostridium botulinum* in a medium composition for culturing *Clostridium botulinum* containing a potato peptone, a yeast extract and glucose, and (b) recovering the botulinum toxin." should be -- "Accordingly, in another aspect, the present invention is directed to a method of preparing a botulinum toxin comprising (a) producing a botulinum toxin by culturing *Clostridium botulinum* in a medium composition for culturing *Clostridium botulinum* containing a potato peptone, a yeast extract and glucose, and (b) recovering the botulinum toxin. --.

Column 4, Line 57, "3% (w/v) ," should be -- 3% (w/v), --.

Column 7, Line 19, "El" should be -- E1 --.

Column 7, Line 26, "10632" should be -- T0632 --.

Column 7, Line 53, "0.2 pm" should be -- 0.2 μm --.

Signed and Sealed this
Fourth Day of February, 2025

Coke Morgan Stewart
*Acting Director of the United States Patent and Trademark Office*